(12) United States Patent
Mou et al.

(10) Patent No.: US 11,614,082 B2
(45) Date of Patent: Mar. 28, 2023

(54) SLIM-TYPE GAS TRANSPORTATION DEVICE

(71) Applicant: Microjet Technology Co., Ltd., Hsinchu (TW)

(72) Inventors: Hao-Jan Mou, Hsinchu (TW); Chung-Wei Kao, Hsinchu (TW); Shih-Chang Chen, Hsinchu (TW); Jia-Yu Liao, Hsinchu (TW); Chih-Feng Lin, Hsinchu (TW); Yung-Lung Han, Hsinchu (TW); Chi-Feng Huang, Hsinchu (TW); Chun-Yi Kuo, Hsinchu (TW)

(73) Assignee: Microjet Technology Co., Ltd., Hsinchu (TW)

( * ) Notice: Subject to any disclaimer, the term of this patent is extended or adjusted under 35 U.S.C. 154(b) by 378 days.

(21) Appl. No.: 17/090,000

(22) Filed: Nov. 5, 2020

(65) Prior Publication Data
US 2021/0199382 A1    Jul. 1, 2021

(30) Foreign Application Priority Data
Dec. 31, 2019    (TW) .................................. 108148731

(51) Int. Cl.
*F04B 45/047*    (2006.01)
*F04B 39/10*    (2006.01)
(Continued)

(52) U.S. Cl.
CPC ........ *F04B 45/047* (2013.01); *F04B 39/1073* (2013.01); *F04B 49/24* (2013.01);
(Continued)

(58) Field of Classification Search
CPC ...... F04B 45/047; F04B 43/046; F04B 49/24; F04B 53/06; F04B 39/1073
See application file for complete search history.

(56) References Cited

U.S. PATENT DOCUMENTS 11,525,439 B2 * 12/2022 Mou ..................... F04B 43/046
2017/0218942 A1 * 8/2017 Chen ................... F16K 99/0015
(Continued)

FOREIGN PATENT DOCUMENTS

CN    104234986 A       12/2014
CN    104246228 A   *   12/2014
(Continued)

*Primary Examiner* — Charles G Freay
(74) *Attorney, Agent, or Firm* — Birch, Stewart, Kolasch & Birch, LLP

(57) ABSTRACT

A slim-type gas transportation device includes a slim-type gas pump and a slim-type valve structure. The slim-type valve structure includes a first thin plate, a valve frame, a valve plate and a second thin plate. The first thin plate has a hollow portion. The valve plate is disposed within an accommodation space of the valve frame. The valve plate includes a valve opening. The valve opening is not aligned with the hollow portion. The second thin plate includes a gas outlet surface, a pressure relief surface, a gas outlet groove, an outlet aperture, a pressure relief hole and a pressure relief trench. The outlet aperture is hollowed out from the gas outlet groove to the pressure relief surface and corresponding in position to the valve opening. The pressure relief hole is spaced apart from the gas outlet groove. The pressure relief trench is concavely formed from the pressure relief surface.

17 Claims, 15 Drawing Sheets

(51) Int. Cl.
  *H01L 41/09*   (2006.01)
  *F04B 49/24*   (2006.01)
  *F04B 53/06*   (2006.01)
  *A61B 5/022*   (2006.01)

(52) U.S. Cl.
  CPC .......... *H01L 41/0973* (2013.01); *A61B 5/022* (2013.01); *F04B 53/06* (2013.01)

(56) References Cited

U.S. PATENT DOCUMENTS

2018/0291887 A1* 10/2018 Mou ................. F04B 49/22
2018/0331276 A1* 11/2018 Liao ................. H01L 41/053
2019/0067550 A1*  2/2019 Mou ................. H01L 41/0973

FOREIGN PATENT DOCUMENTS

| CN | 108884823 | A | 11/2018 |
|----|-----------|---|---------|
| CN | 109745023 | A | 5/2019 |
| CN | 209018718 | U | 6/2019 |
| EP | 3 321 506 | A1 | 5/2018 |

\* cited by examiner

SLIM-TYPE GAS TRANSPORTATION DEVICE

FIELD OF THE INVENTION

The present invention relates to a slim-type gas transportation device, and more particularly to a slim-type gas transportation device formed by stacking a plurality of thin plates.

BACKGROUND OF THE INVENTION

With the rapid advancement of science and technology, the application of gas transportation device tends to be more and more diversified. For the industrial applications, the biomedical applications, the healthcare, the electronic cooling and so on, even the most popular wearable devices, the gas transportation device is utilized therein. It is obviously that the conventional gas transportation devices gradually tend to miniaturize and thin the structure and maximize the flow rate thereof.

At present, the gas transportation device has a specified thickness. Since it is difficult to reduce the thickness of the valve structure of the gas transportation device, the overall thickness of the gas transportation device is too large. Consequently, it is difficult to combine the gas transportation device with a portable electronic device. Therefore, how to make the gas transportation device thinner to be combined with the portable electronic device is a problem that urgently needs to be solved.

SUMMARY OF THE INVENTION

The present invention provides a slim-type gas transportation device. The slim-type gas transportation device includes a slim-type gas pump and a slim-type valve structure. The slim-type valve structure includes thin metal plates. Consequently, the thickness of the slim-type gas transportation device is reduced significantly.

In accordance with an aspect of the present invention, a slim-type gas transportation device is provided. The slim-type gas transportation device includes a slim-type gas pump and a slim-type valve structure. The slim-type gas pump includes a gas inlet plate, a resonance plate, an actuator, a first insulation frame, a conducting frame and a second insulation frame. The gas inlet plate has a first surface, a second surface, a plurality of inlet apertures, a convergence chamber and a plurality of inlet grooves. The first surface and the second surface are opposed to each other. The plurality of inlet apertures run through the first surface and the second surface. The convergence chamber is concavely formed from the second surface and located at a center of the second surface. The inlet grooves are concavely formed from the second surface. Each of the plurality of inlet grooves has an end in communication with the inlet aperture corresponding thereto and the other end in communication with the convergence chamber. The resonance plate is combined with the second surface of the gas inlet plate. The resonance plate includes a central aperture, a vibration part and a fixed part. The central aperture is located at a center of the resonance plate. The vibration part surrounds the central aperture and is corresponding in position to the convergence chamber. The fixed part surrounds the vibration part. The resonance plate is combined with the gas inlet plate through the fixed part. The actuator is combined with the fixed part of the resonance plate. The first insulation frame is combined with the actuator. The conducting frame is combined with the first insulation frame. The second insulation frame is combined with the conducting frame. The slim-type valve structure is combined with the second insulation frame. The slim-type valve structure includes a first thin plate, a valve frame, a valve plate and a second thin plate. The first thin plate has a hollow portion. The valve frame has an accommodation space. The valve plate is disposed within the accommodation space and has a valve opening. The valve opening is not aligned to the hollow portion. The second thin plate includes a gas outlet surface, a pressure relief surface, a gas outlet groove, an outlet aperture, a pressure relief hole and a pressure relief trench. The gas outlet surface and the pressure relief surface are opposed to each other. The gas outlet groove is concavely formed from the gas outlet surface and partially aligned to the hollow portion of the first thin plate. The outlet aperture is hollowed out from the gas outlet groove to the pressure relief surface and corresponding in position to the valve opening of the valve plate. The pressure relief hole is spaced apart from the gas outlet groove. The pressure relief trench is concavely formed from the pressure relief surface and in communication with the pressure relief hole. The first thin plate, the valve frame and the second thin plate are stacked on each other sequentially.

The above contents of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
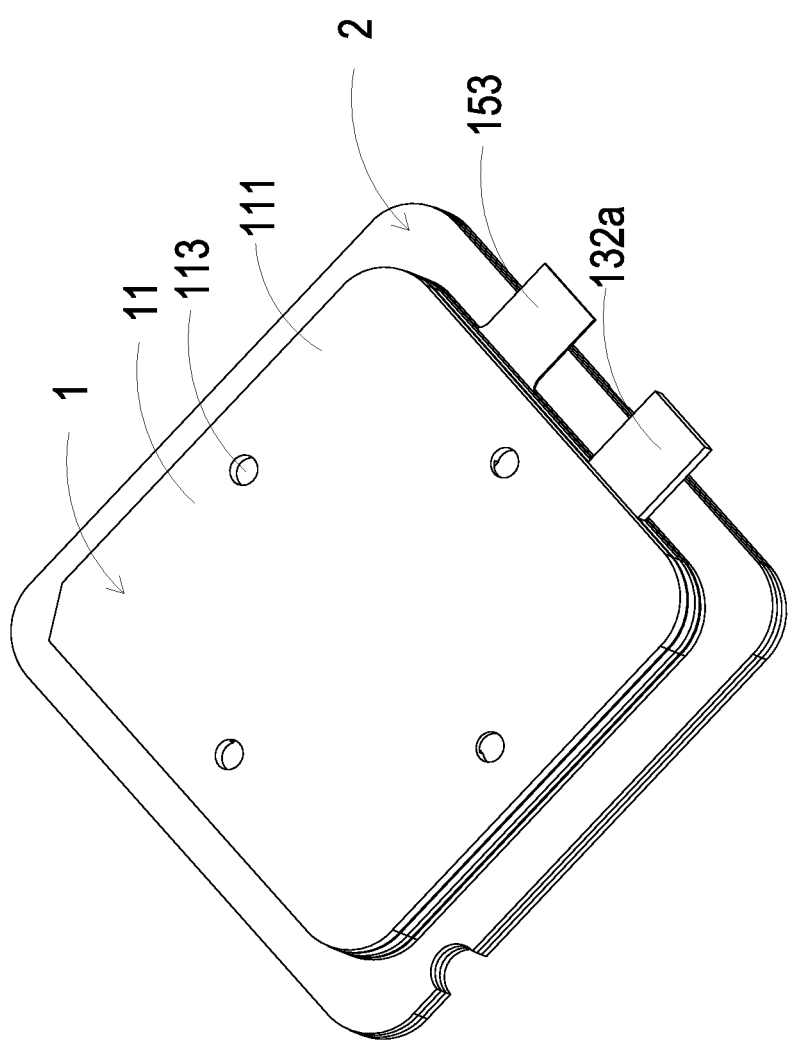
FIG. 1A is a schematic perspective view illustrating a slim-type gas transportation device according to an embodiment of the present invention.
Figure 1B:
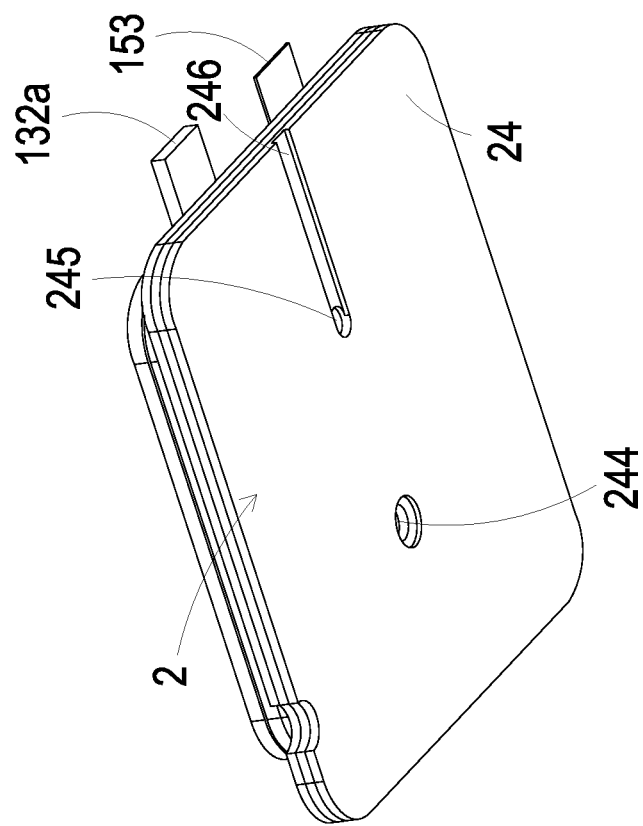
FIG. 1B is a schematic perspective view illustrating the slim-type gas transportation device as shown in FIG. 1A and taken along another viewpoint.

Please refer to FIGS. 1A and 1B. FIG. 1A is a schematic perspective view illustrating a slim-type gas transportation device according to an embodiment of the present invention. FIG. 1B is a schematic perspective view illustrating the slim-type gas transportation device as shown in FIG. 1A and taken along another viewpoint. The slim-type gas transportation device 100 includes a slim-type gas pump 1 and a slim-type valve structure 2. The slim-type gas pump 1 is stacked on the slim-type valve structure 2.

Figure 2A:
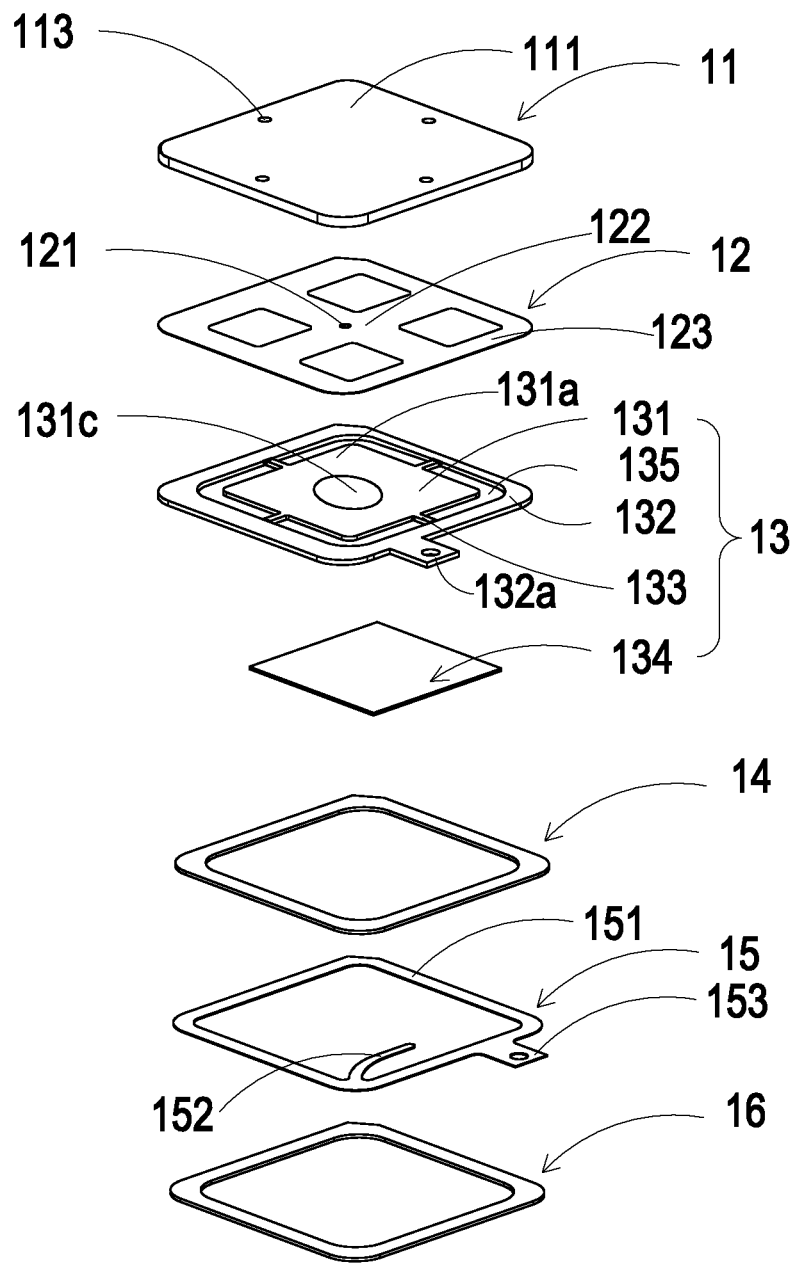
FIG. 2A is a schematic exploded view illustrating the slim-type gas pump of the slim-type gas transportation device according to the embodiment of the present invention.
Figure 2B:
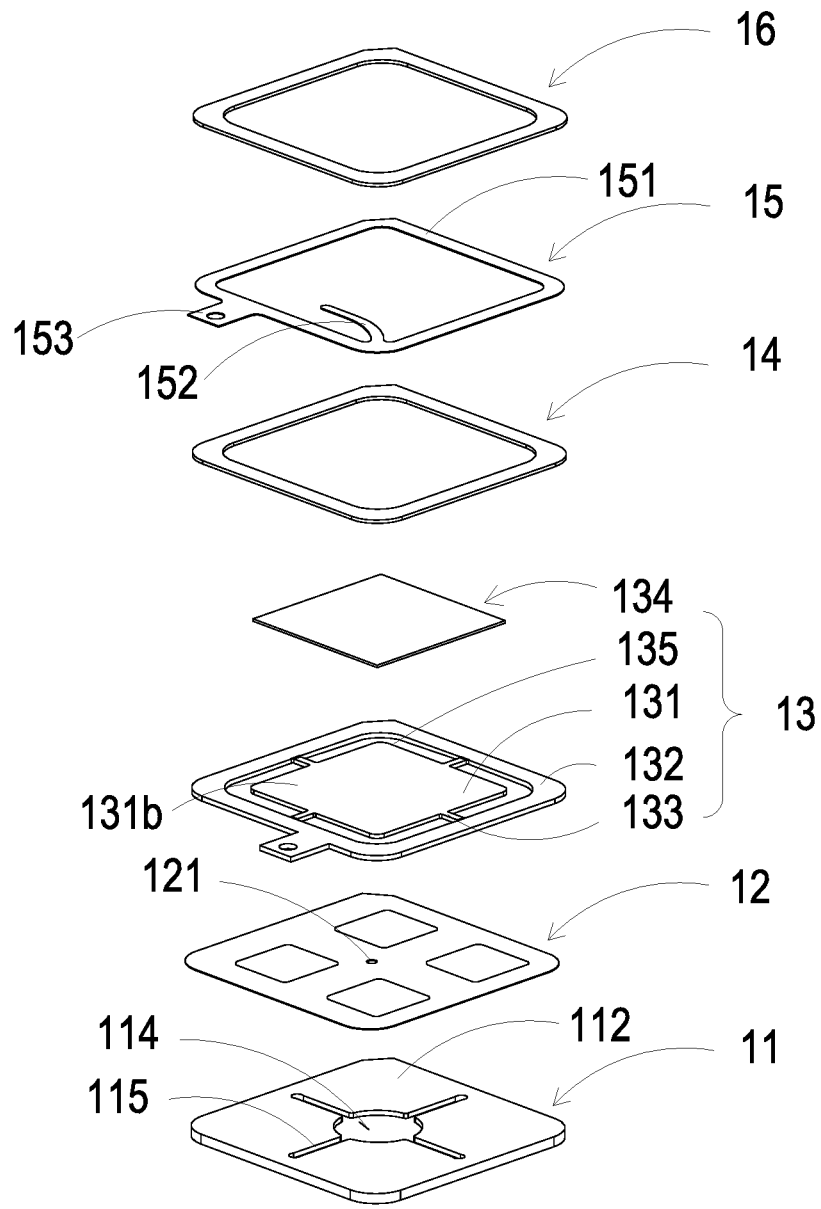
FIG. 2B is a schematic exploded view illustrating the slim-type gas pump as shown in FIG. 2A and taken along another viewpoint.

Please refer to FIGS. 2A and 2B. FIG. 2A is a schematic exploded view illustrating the slim-type gas pump of the slim-type gas transportation device according to the embodiment of the present invention. FIG. 2B is a schematic exploded view illustrating the slim-type gas pump as shown in FIG. 2A and taken along another viewpoint. The slim-type gas pump 1 includes a gas inlet plate 11, a resonance plate 12, an actuator 13, a first insulation frame 14, a conducting frame 15 and a second insulation frame 16.

The gas inlet plate 11 has a first surface 111, a second surface 112, a plurality of inlet apertures 113, a convergence chamber 114 and a plurality of inlet grooves 115. The first surface 111 and the second surface 112 are opposed to each other. In this embodiment, the gas inlet plate 11 has four inlet apertures 113. The present disclosure is not limited thereto. The inlet apertures 113 run through the gas inlet plate 11 from the first surface 111 to the second surface 112. The convergence chamber 114 is concavely formed from the second surface 112 and located at a center of the second surface 112. The number and arrangement of the inlet grooves 115 correspond to that of the inlet apertures 113. In this embodiment, the gas inlet plate 11 has four inlet grooves 115. Each inlet groove 115 has an end in fluid communication to the inlet aperture 113 corresponding thereto and the other end in fluid communication to the convergence chamber 114. Thus, the gas inhaled into the inlet grooves 115 through respective inlet apertures 113 is transported and converged into the convergence chamber 114.

The resonance plate 12 is attached to the second surface 112 of the gas inlet plate 11. The resonance plate 32 has a central aperture 121, a vibration part 122 and a fixed part 123. The central aperture 121 runs through a center of the resonance plate 12. The vibration part 122 surrounds the central aperture 121. The fixed part 123 surrounds the vibration part 122. The resonance plate 12 is combined with the gas inlet plate 11 through the fixed part 123. When the resonance plate 12 is combined with the gas inlet plate 11, the central aperture 121 and the vibration part 122 of the resonance plate 12 are aligned to the convergence chamber 114 of the gas inlet plate 11 along the vertical direction.

The actuator 13 is combined with the resonance plate 12. The actuator 13 includes a vibration plate 131, an outer frame 132, a plurality of connecting parts 133, a piezoelectric element 134 and a plurality of gas channels 135. The vibration plate 131 is a square shape. The outer frame 132 is a square frame that is disposed around the vibration plate 131. The outer frame 132 has a first conducting pin 132a protruding outwardly from an outer edge of the outer frame 131 along the horizontal direction. The plurality of gas channels 135 are formed among the vibration plate 131, the outer frame 132 and the plurality of connecting parts 133. The actuator 13 is combined with the fixed part 123 of the resonance plate 12 through the outer frame 132. In this embodiment, the actuator 13 includes four connecting parts 133. The present disclosure is not limited thereto. The connecting parts 133 are connected between the vibration plate 131 and the outer frame 132 for elastically supporting the vibration plate 131. The shape and the area of the piezoelectric element 134 match the shape and the area of the vibration plate 131. In an embodiment, the piezoelectric element 134 is a square shape. Preferably but not exclusively, a length of a side of the piezoelectric element 134 is smaller than or equal to a length of a side of the vibration plate 131. The piezoelectric element 134 is attached to the vibration plate 131. In addition, the vibration plate 131 has a top surface 131a and a bottom surface 131b, which are opposed to each other. The vibration plate 131 further includes a bulge 131c disposed on the top surface 131a of the vibration plate 131. The piezoelectric element 134 is attached to the bottom surface 131b of the vibration plate 131.

The profiles of the first insulation frame 14 and the second insulation frame 16 match the profile of the outer frame 132 of the actuator 13. That is, the first insulation frame 14 and the second insulation frame 16 are square frames. The conducting frame 15 includes a frame body 151, an electrode part 152 and a second conducting pin 153. The profile of the frame body 151 matches the profiles of the first insulation frame 14 and the second insulation frame 16. That is, the frame body 151 is a square frame. The electrode part 152 is curvedly protruding from an inner edge of the frame body 151 toward a center of the frame body 151. The second conducting pin 153 is protruding outwardly from an outer edge of the frame body 151 along the horizontal direction.

Figure 3A:
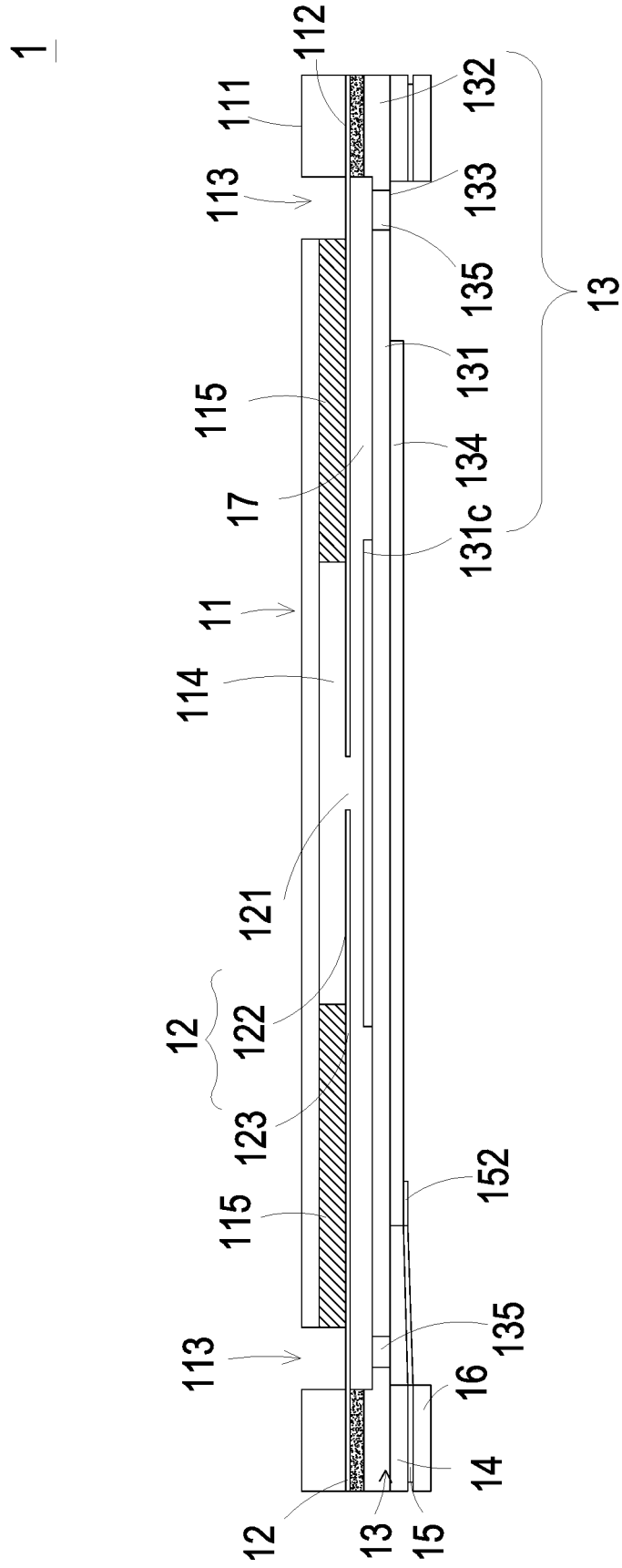
FIG. 3A is a schematic cross-sectional view illustrating the slim-type gas pump of the slim-type gas transportation device according to the embodiment of the present invention.

Please refer to FIGS. 3A and 2A. FIG. 3A is a schematic cross-sectional view illustrating the slim-type gas pump of the slim-type gas transportation device according to the embodiment of the present invention. The gas inlet plate 11, the resonance plate 12, the actuator 13, the first insulation frame 14, the conducting frame 15 and the second insulation frame 16 are stacked on each other sequentially. A vibration chamber 17 is formed between the resonance plate 12 and the actuator 13. In addition, the electrode part 152 of the conducting frame 15 is in contact with the piezoelectric element 134 of the actuator 13 and electrically connected to the piezoelectric element 134, so that the first conducting pin 132a of the actuator 13 and the second conducting pin 153 of the conducting frame 15 can receive a driving signal (including a driving voltage and a driving frequency) from an external circuit (not shown) and transmit the driving signal to the piezoelectric element 134.

Figure 3B:
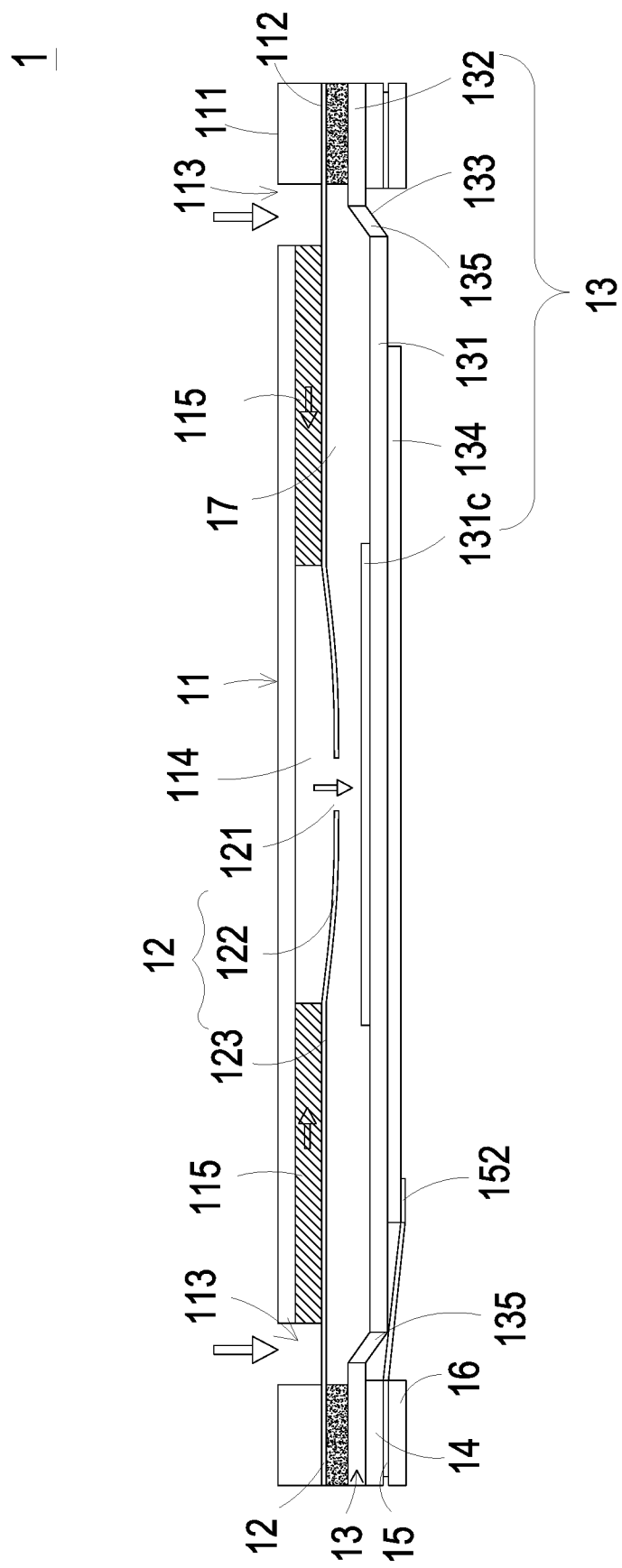
FIGS. 3B to 3D schematically illustrate the operations of the slim-type gas pump of the slim-type gas transportation device according to the embodiment of the present invention.
Figure 3C:
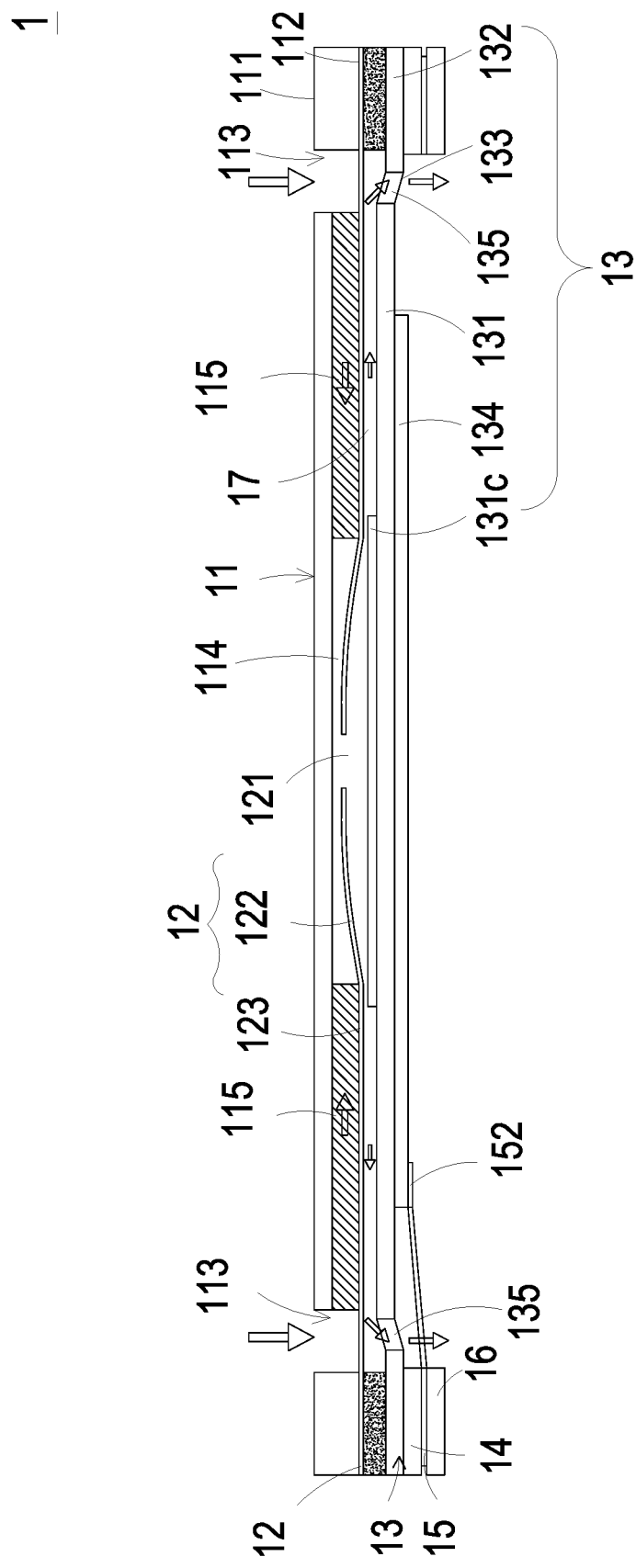
Figure 3D:
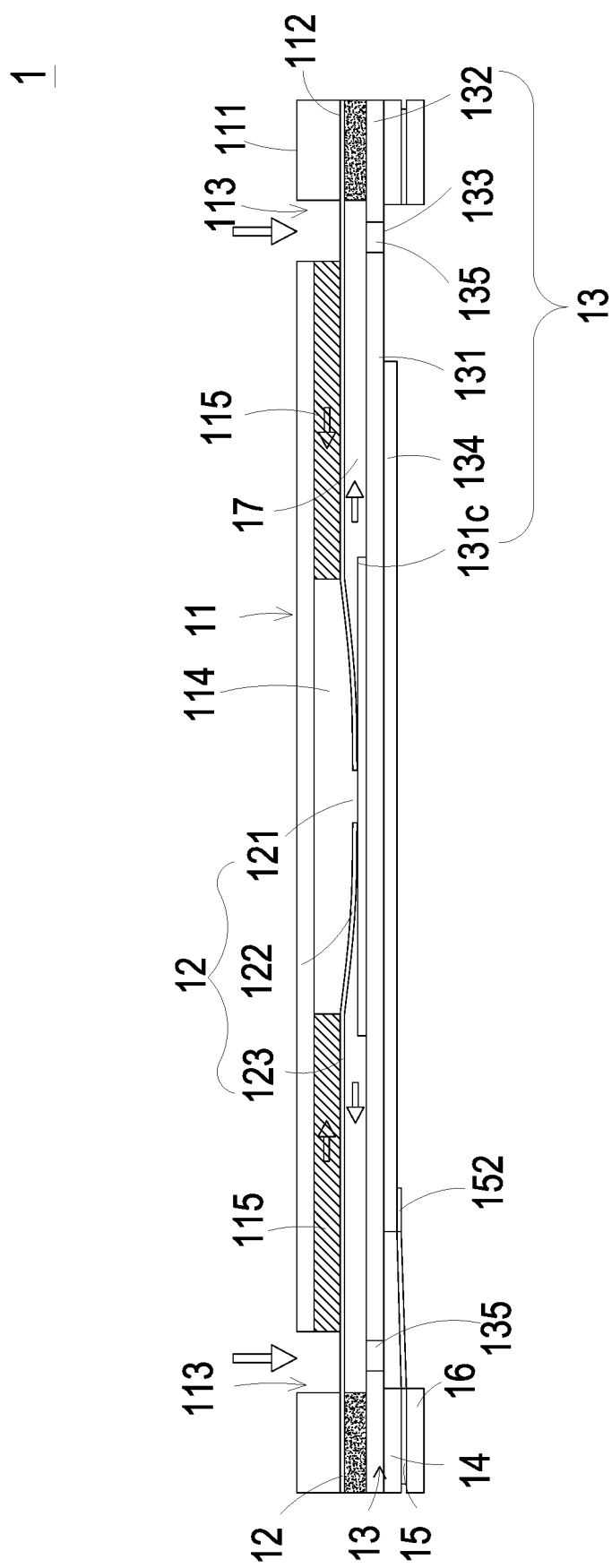

FIGS. 3B to 3D schematically illustrate the operations of the slim-type gas pump of the slim-type gas transportation device according to the embodiment of the present invention. When the piezoelectric element 134 receives the driving signal, the piezoelectric element 134 deforms in response to a piezoelectric effect to drive the vibration plate 131 to move upwardly or downwardly. Please refer to FIG. 3B. When the vibration plate 131 is driven to move downwardly, the vibration part 122 of the resonance plate 12 correspondingly moves downwardly, so that the volume of the convergence chamber 114 is increased. The ambient gas is inhaled into the convergence chamber 114 through the inlet apertures 113 and the inlet grooves 115. Please refer to FIG. 3C. When the vibration plate 131 is driven to move upwardly, the gas in the vibration chamber 17 is pushed from a center of the vibration chamber 17 to the peripheral regions of the vibration chamber 17, transported through the gas channels 135, and transported downwardly. Meanwhile, the resonance plate 12 moves upwardly, the gas in the convergence chamber 114 is pushed downwardly through the central aperture 121. Please refer to FIG. 3D. When the vibration plate 131 is driven to move downwardly and returned to its original position, the vibration part 122 of the resonance plate 12 is synchronously moved downwardly. The vibration part 122 is close to the bulge 131c of the vibration plate 13, so that the gas in the vibration chamber 17 is pushed to the gas channels 135. As the vibration part 122 moves downwardly, the volume of the convergence chamber 114 is expanded, so that the ambient gas is inhaled into the convergence chamber 114 through the inlet apertures 113 and the inlet groove 115. By repeating the above steps, the gas is continuously transported downwardly to the slim-type valve structure 2.

Figure 4A:
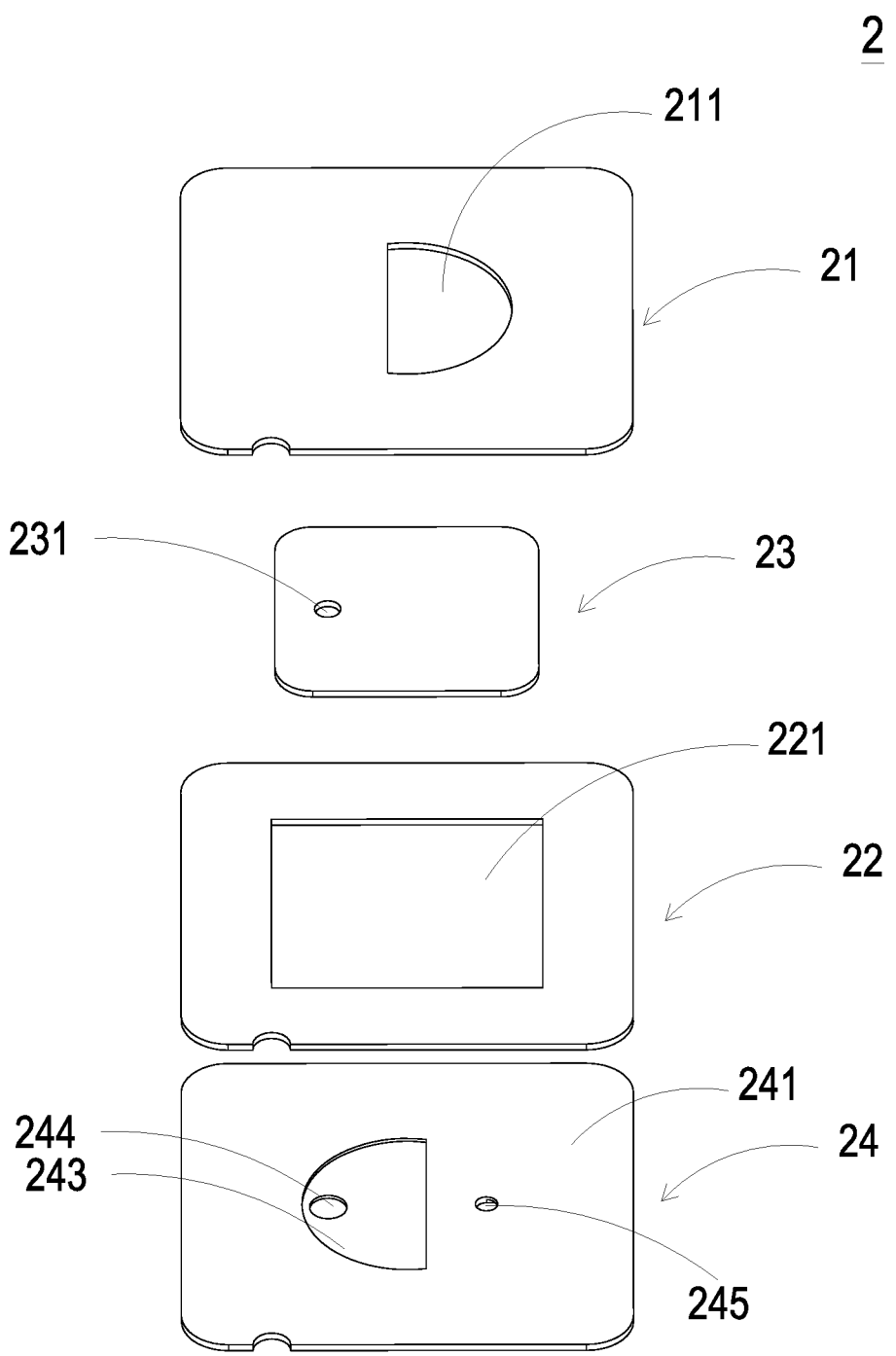
FIG. 4A is a schematic exploded view illustrating the slim-type valve structure of the slim-type gas transportation device according to the embodiment of the present invention.
Figure 4B:
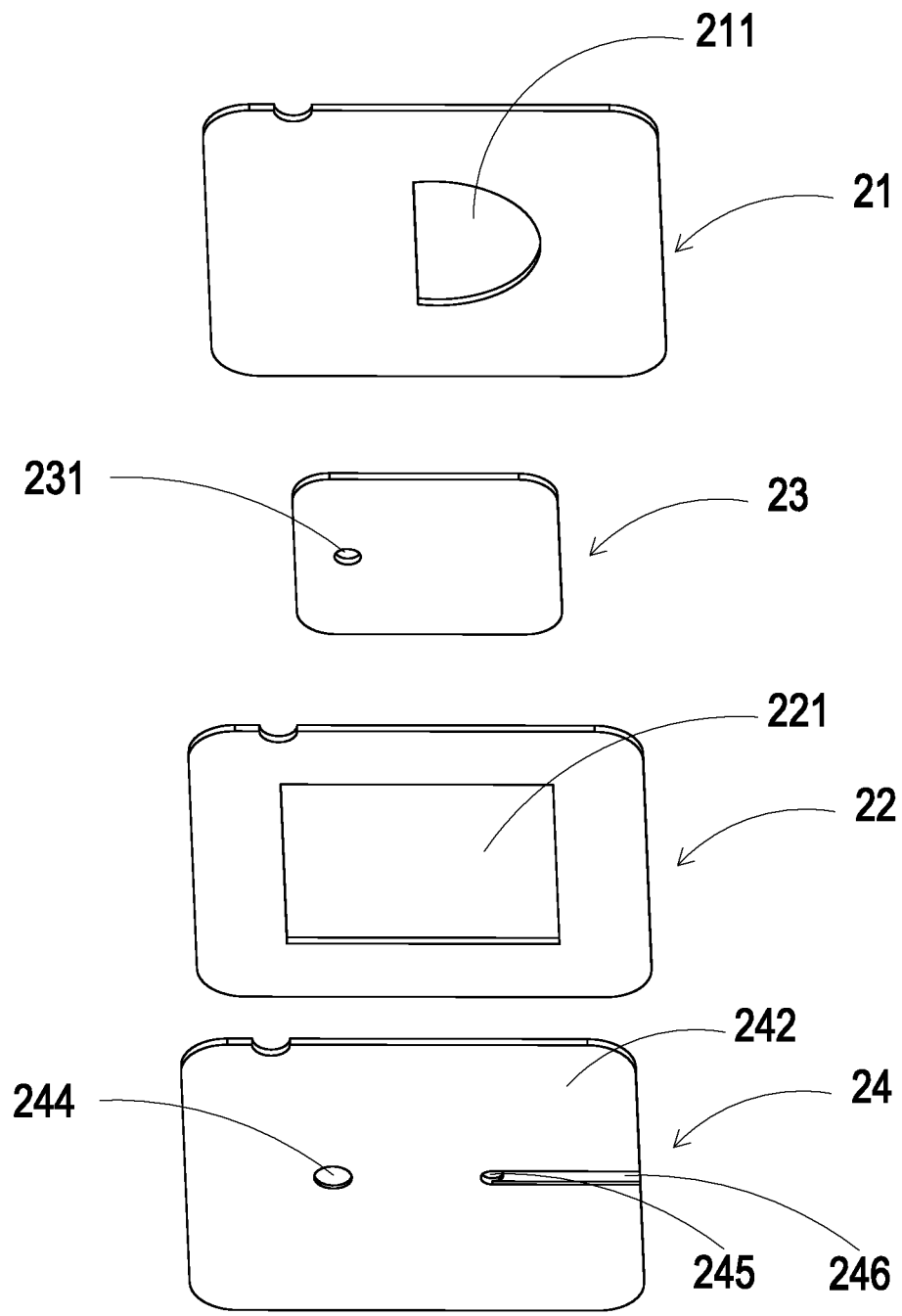
FIG. 4B is a schematic exploded view illustrating the slim-type valve structure as shown in FIG. 4A and taken along another viewpoint.

Please refer to FIGS. 4A and 4B. FIG. 4A is a schematic exploded view illustrating the slim-type valve structure of the slim-type gas transportation device according to the embodiment of the present invention. FIG. 4B is a schematic exploded view illustrating the slim-type valve structure as shown in FIG. 4A and taken along another viewpoint. The slim-type valve structure 2 includes a first thin plate 21, a valve frame 22, a valve plate 23 and a second thin plate 24.

The first thin plate 21 has a hollow portion 211. The valve frame 22 has an accommodation space 221. The valve plate 23 is disposed within the accommodation space 221 and has a valve opening 231. The valve opening 231 and the hollow portion 211 are not aligned with each other. The profile of the accommodation space 221 matches the profile of the valve plate 23, so that the valve plate 23 can be fixed and positioned in the accommodation space 221.

The second thin plate 24 includes a gas outlet surface 241, a pressure relief surface 242, a gas outlet groove 243, an outlet aperture 244, a pressure relief hole 245 and a pressure relief trench 246. The gas outlet surface 241 and the pressure relief surface 242 are opposed to each other. The gas outlet groove 243 is concavely formed from the gas outlet surface 241 and is partially aligned to the hollow portion 211 of the first thin plate 21. The outlet aperture 244 is hollowed out from the gas outlet groove 243 to the pressure relief surface 242, and is corresponding in position to the valve opening 231 of the valve plate 23. Moreover, the diameter of the outlet aperture 244 is greater than the diameter of the valve opening 231. The pressure relief hole 245 is spaced apart from the gas outlet groove 243. The pressure relief trench 246 is concavely formed from the pressure relief surface 242. The pressure relief trench 246 has an end in fluid communication with the pressure relief hole 245 and the other end extending to the edge of the second thin plate 24. In an embodiment, the profile of the gas outlet groove 243 of the second thin plate 24 and the profile of the hollow portion 211 of the first thin plate 21 are identical and match with each other.

In an embodiment, each of the first thin plate 21, the valve frame 22 and the second thin plate 24 is made of a metallic material. Preferably, the first thin plate 21, the valve frame 22 and the second thin plate 24 are made of the same metallic material (e.g., stainless steel). Moreover, the first thin plate 21, the valve frame 22 and the second thin plate 24 have the same thickness (e.g., 2 mm).

Figure 5A:
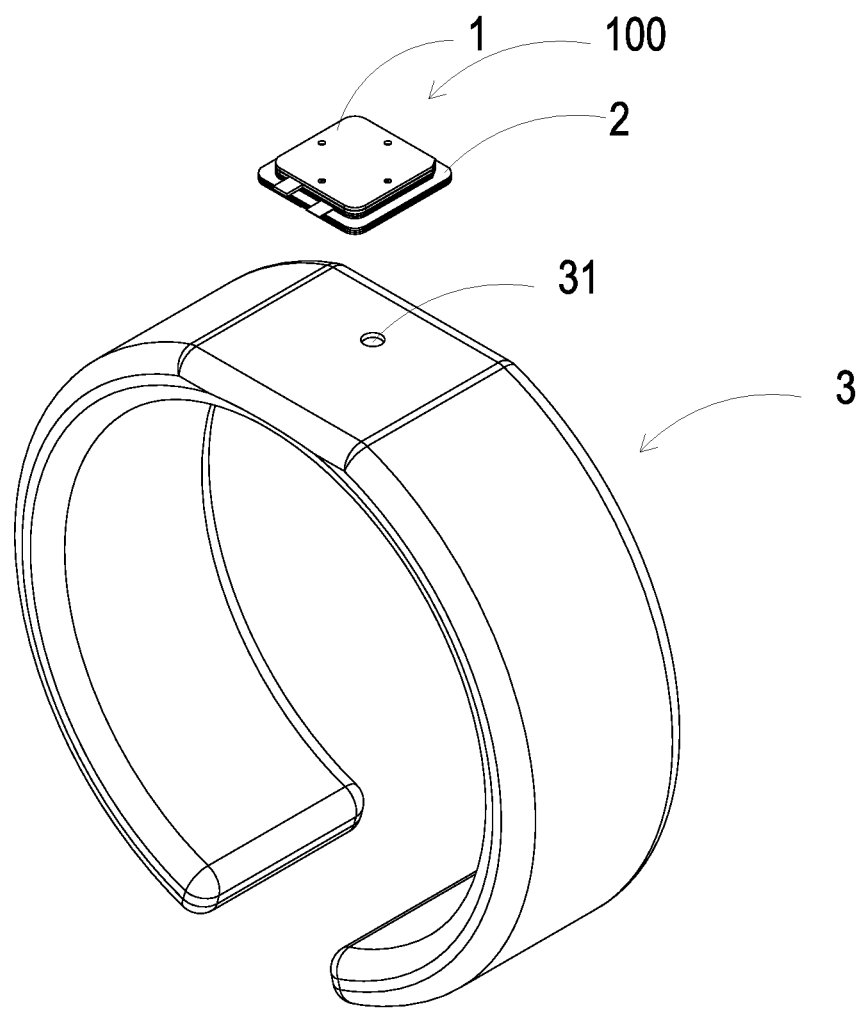
FIG. 5A schematically illustrates the applications of the slim-type gas transportation device on an air bag.
Figure 5B:
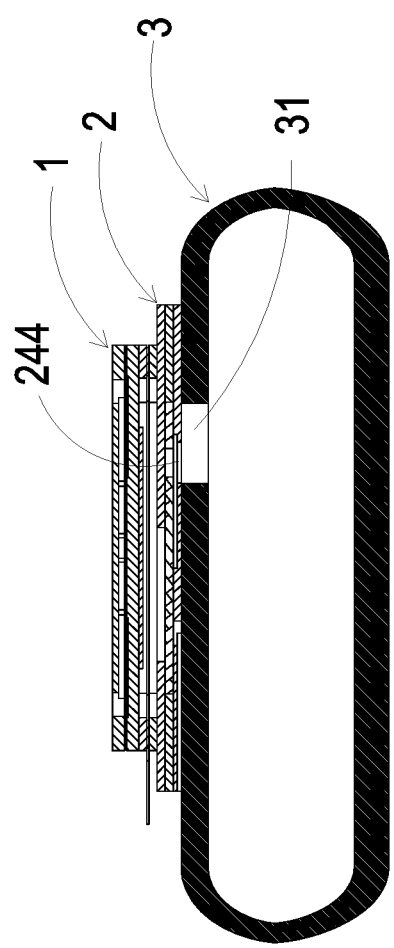
FIG. 5B is a schematic cross-sectional view illustrating the combination of the slim-type gas transportation device and the air bag.

Please refer to FIGS. 5A and 5B. FIG. 5A schematically illustrates the applications of the slim-type gas transportation device on an air bag. FIG. 5B is a schematic cross-sectional view illustrating the combination of the slim-type gas transportation device and the air bag. As shown in FIGS. 5A and 5B, the second thin plate 24 of the slim-type gas transportation device 100 is combined with an air bag 3. The air bag 3 has an air port 31. The air port 31 is in fluid communication with the outlet aperture 244 of the second thin plate 24. When the slim-type gas transportation device 100 is actuated, the gas is transported from the slim-type gas transportation device 100 to the air bag 3. In an embodiment, the air bag 3 is a ring-shaped air bag. The present disclosure is not limited thereto.

Figure 6A:
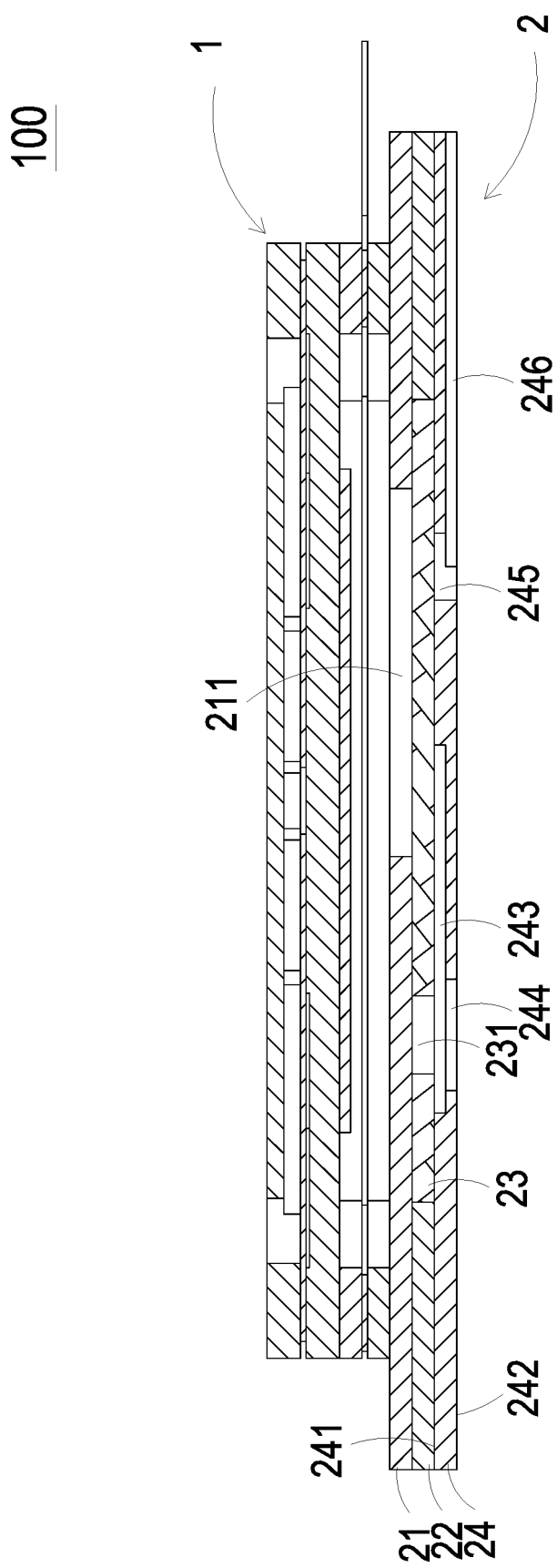
FIG. 6A is a schematic cross-sectional view illustrating the structure of the slim-type gas transportation device.
Figure 6B:
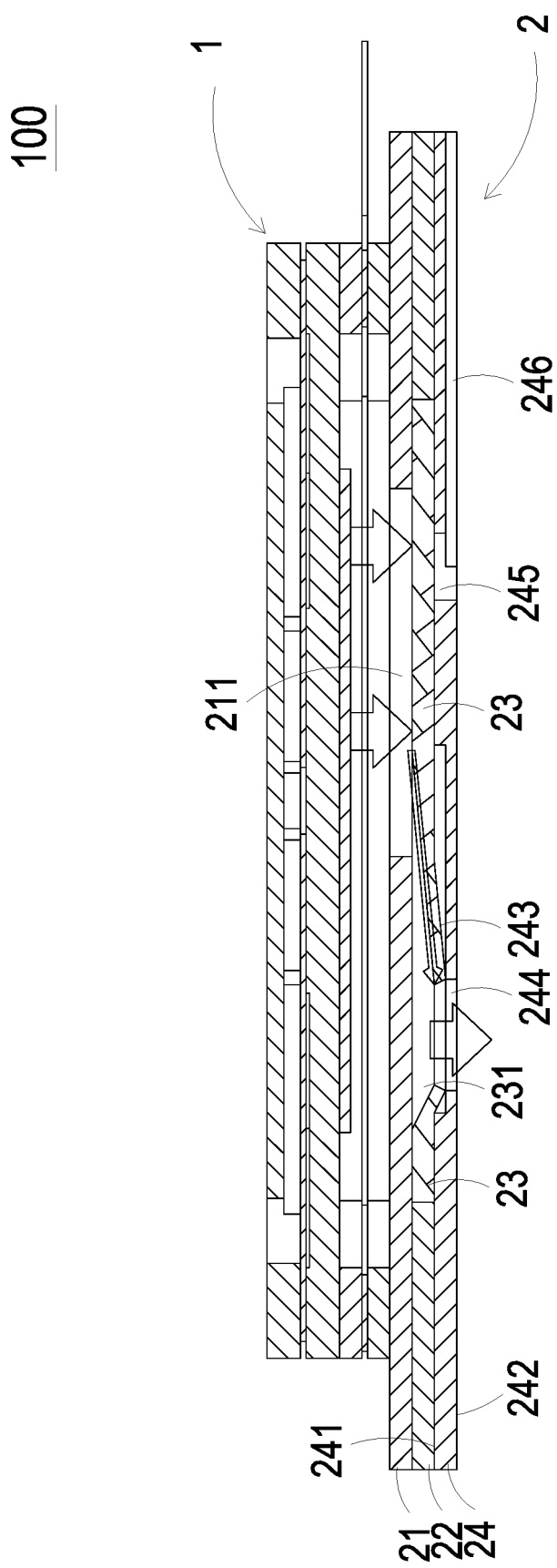
FIG. 6B is a schematic cross-sectional view illustrating the gas-discharging operation of the slim-type gas transportation device.
Figure 6C:
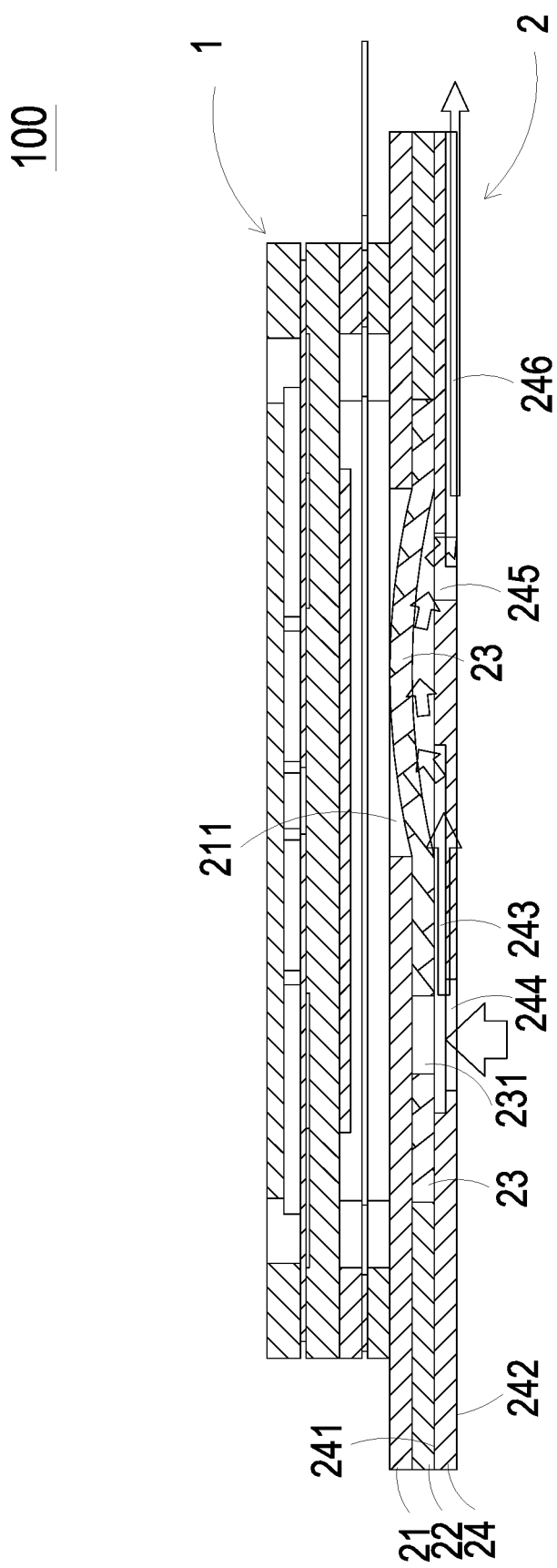
FIG. 6C is a schematic cross-sectional view illustrating the pressure-releasing operation of the slim-type gas transportation device.

Please refer to FIG. 6A, which is a schematic cross-sectional view illustrating the structure of the slim-type gas transportation device. The first thin plate 21, the valve frame 22 and the second thin plate 24 of the slim-type value structure 2 are stacked on each other sequentially. The valve plate 23 is disposed within the accommodation space 221 of the valve frame 22. The slim-type gas pump 1 is stacked on the slim-type valve structure 2. As shown in FIG. 6B, when the gas is transported from the slim-type gas pump 1 to the slim-type valve structure 2, the gas is introduced into the hollow portion 211 of the first thin plate 21 to push the valve plate 23. Meanwhile, partial region of the valve plate 23 over the gas outlet groove 243 is pushed downwardly, so that the gas flows into the gas outlet groove 243, is transported through the valve opening 231 of the valve plate 23, and is discharged through the outlet aperture 244 of the second thin plate 24. FIG. 6C is a schematic cross-sectional view illustrating the pressure-releasing operation of the slim-type gas transportation device. As the slim-type gas transportation device 100 stops transporting the gas to the air bag 3, the internal pressure of the air bag 3 is greater than the external pressure. Meanwhile, the pressure-releasing operation of the slim-type gas transportation device 100 may be performed through the slim-type valve structure 2. Please refer to FIG. 6C and details are described below. The gas is transported back to the second thin plate 24 through the outlet aperture 244 to push the valve plate 23 upwardly. Therefore, the valve opening 231 of the valve plate 23 is closed by the first thin plate 21, and meanwhile the portion of the valve plate 23 corresponding to the hollow portion 211 of the first thin plate 21 is pushed upwardly. In this way, the gas may flow into the hollow portion 211 of the first thin plate 21 through the gas outlet groove 243, and then flows along the pressure relief trench 246 through the pressure relief hole 245. The gas is thereby discharged from the air bag 3, and thus the pressure-releasing operation is completed.

From the above descriptions, the present invention provides a slim-type gas transportation device. By using a slim-type valve structure including a first thin plate, a valve frame, a valve plate and a second thin plate, the overall thickness of the slim-type gas transportation device is reduced significantly. Since the thickness of each of the first thin plate, the valve frame and the second thin plate is reduced to 2 mm, the overall thickness of the slim-type valve structure is only 6 mm. Since the first thin plate, the valve frame and the second thin plate are made of the metallic material, the overall rigidity of the slim-type gas transportation device is largely increased and the heat dissipation efficacy of the slim-type gas transportation device is enhanced.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A slim-type gas transportation device, comprising:
    a slim-type gas pump comprising:
        a gas inlet plate comprising:
            a first surface;
            a second surface opposed to the first surface;
            a plurality of inlet apertures running through the first surface and the second surface;
            a convergence chamber concavely formed from the second surface and located at a center of the second surface; and
            a plurality of inlet grooves concavely formed from the second surface, wherein each of the plurality of inlet grooves has an end in communication with the inlet aperture corresponding thereto and the other end in communication with the convergence chamber;
        a resonance plate combined with the second surface of the gas inlet plate, and comprising:
            a central aperture located at a center of the resonance plate;
            a vibration part surrounding around the central aperture and corresponding in position to the convergence chamber; and
            a fixed part surrounding around the vibration part, wherein the resonance plate is combined with the gas inlet plate through the fixed part;
        an actuator combined with the fixed part of the resonance plate;
        a first insulation frame combined with the actuator;
        a conducting frame combined with the first insulation frame; and
        a second insulation frame combined with the conducting frame; and
    a slim-type valve structure combined with the second insulation frame, and comprising:
        a first thin plate having a hollow portion;
        a valve frame having an accommodation space;
        a valve plate disposed within the accommodation space and having a valve opening, wherein the valve opening is not aligned to the hollow portion; and
        a second thin plate comprising:
            a gas outlet surface;
            a pressure relief surface opposed to the gas outlet surface;
            a gas outlet groove concavely formed from the gas outlet surface and partially aligned to the hollow portion of the first thin plate;
            an outlet aperture hollowed out from the gas outlet groove to the pressure relief surface and corresponding in position to the valve opening of the valve plate;
            a pressure relief hole spaced apart from the gas outlet groove; and
            a pressure relief trench concavely formed from the pressure relief surface and in communication with the pressure relief hole,
        wherein the first thin plate, the valve frame and the second thin plate are stacked on each other sequentially.

2. The slim-type gas transportation device according to claim 1, wherein the first thin plate, the valve frame and the second thin plate have a same thickness.

3. The slim-type gas transportation device according to claim 1, wherein the actuator comprises:
    a vibration plate being a square shape;
    an outer frame arranged around the vibration plate;
    a plurality of connecting parts connected between the vibration plate and the outer frame for elastically supporting the vibration plate; and
    a piezoelectric element attached to the vibration plate, wherein a shape and an area of the piezoelectric element match a shape and an area of the vibration plate.

4. The slim-type gas transportation device according to claim 3, wherein the first thin plate, the valve frame and the second thin plate have a same thickness.

5. The slim-type gas transportation device according to claim 1, wherein a diameter of the outlet aperture is greater than a diameter of the valve opening.

6. The slim-type gas transportation device according to claim 5, wherein the first thin plate, the valve frame and the second thin plate have a same thickness.

7. The slim-type gas transportation device according to claim 5, wherein the first thin plate, the valve frame and the second thin plate are made of a metallic material.

8. The slim-type gas transportation device according to claim 7, wherein the first thin plate, the valve frame and the second thin plate have a same thickness.

9. The slim-type gas transportation device according to claim 7, wherein the metallic material is stainless steel.

10. The slim-type gas transportation device according to claim 9, wherein the first thin plate, the valve frame and the second thin plate have a same thickness.

11. The slim-type gas transportation device according to claim 1, wherein a profile of the hollow portion and a profile of the gas outlet groove are identical.

12. The slim-type gas transportation device according to claim 11, wherein the first thin plate, the valve frame and the second thin plate have a same thickness.

13. The slim-type gas transportation device according to claim 1, wherein the second thin plate is combined with an air bag, wherein the air bag has an air port, and the air port is in communication with the outlet aperture of the second thin plate.

14. The slim-type gas transportation device according to claim 13, wherein the first thin plate, the valve frame and the second thin plate have a same thickness.

15. The slim-type gas transportation device according to claim 13, wherein the air bag is a ring-shaped air bag.

16. The slim-type gas transportation device according to claim 15, wherein the first thin plate, the valve frame and the second thin plate have a same thickness.

17. The slim-type gas transportation device according to claim 1, wherein each of the first thin plate, the valve frame and the second thin plate has a thickness of 2 mm.

* * * * *